(12) United States Patent
Bright-Ellington

(10) Patent No.: US 6,843,983 B2
(45) Date of Patent: Jan. 18, 2005

(54) SHAVING PREPARATIONS AND METHODS FOR THE PREVENTION AND TREATMENT OF PSEUDOFOLLICULITIS BARBAE

(76) Inventor: Virgie Bright-Ellington, 233 E. 86th St., New York, NY (US) 10028

( * ) Notice: Subject to any disclaimer, the term of this patent is extended or adjusted under 35 U.S.C. 154(b) by 31 days.

(21) Appl. No.: 09/875,198

(22) Filed: Jun. 7, 2001

(65) Prior Publication Data

US 2002/0187118 A1 Dec. 12, 2002

(51) Int. Cl.$^7$ .............................. A61K 7/15; A61K 7/00
(52) U.S. Cl. .......................................... 424/73; 424/401
(58) Field of Search ................................... 424/73, 401

(56) References Cited

U.S. PATENT DOCUMENTS

| | | | |
|---|---|---|---|
| 3,898,330 A | * | 8/1975 | McGinity ................... 424/181 |
| 4,228,163 A | | 10/1980 | Bliss |
| 4,944,939 A | * | 7/1990 | Moore .......................... 424/73 |
| 6,001,340 A | | 12/1999 | Rosen et al. |
| 6,352,691 B1 | * | 3/2002 | Ortiz et al. .................... 424/73 |
| 6,375,942 B1 | * | 4/2002 | Rico ....................... 424/78.07 |

FOREIGN PATENT DOCUMENTS

EP WO 86/05389 * 9/1986 ............ A61K/7/00

* cited by examiner

*Primary Examiner*—James M. Spear
(74) *Attorney, Agent, or Firm*—Kenyon & Kenyon

(57) ABSTRACT

Improved shaving preparations for the prevention and treatment of pseudofolliculitis barbae and ingrown hair containing glucocorticoid and an antibacterial agent. Optionally, the shaving preparation may also include a therapeutic amount of benzoyl peroxide. The present invention also provides a method for preventing and/or treating pseudofolliculitis barbae, wherein the shaving preparations of the present invention are applied to the affected area immediately before shaving, during, after or in between shaves.

12 Claims, No Drawings

SHAVING PREPARATIONS AND METHODS FOR THE PREVENTION AND TREATMENT OF PSEUDOFOLLICULITIS BARBAE

FIELD OF THE INVENTION

The present invention relates to improvements in shaving preparations and methods to aid in treatment and prevention of the skin condition pseudofolliculitis barbae, also known as ingrown hair or razor bumps.

BACKGROUND OF THE INVENTION

Pseudofolliculitis barbae (PFB) is a skin condition in which hair tends to become ingrown. As a consequence, a foreign-body type of inflammatory papule or pustule develops, which may then progress into a nodule or abscess. PFB is generally treated by applying a topical therapeutic agent to the infected area. In severe cases of untreated PFB, systemic antibiotics are used to treat secondary bacterial infection. While some of the prior art agents provide some relief by treating the inflammation and infection caused by PFB, they generally do not provide treatment or prevention of PFB.

Most of the therapeutic agents disclosed in the prior art include the use of topical compositions containing ingredients requiring a medical prescription, or drying and acidic agents which cause inflammatory reactions in some with sensitive skin, precluding usage for all skin types. Moreover, the prior art disclosures regarding shaving preparations require multiple treatment steps in addition to shaving. Applicant knows of nothing in the prior art that teaches the use of a shaving preparation of the present invention in a single treatment step prior to shaving.

The shaving preparations of the prior art used for the treatment of PFB have numerous disadvantages. For example the shaving preparations of the prior art must be applied to the affected skin area at least several hours prior to shaving, and require multiple treatment steps, which are impractical and inconvenient requirements. Moreover, the prior art shaving preparations generally require ingredients which cause skin irritations and other harmful side effects.

The shaving preparations of the present invention overcome the problems of the prior art in that, for example, they provide treatment and prevention of PFB without the need for multiple treatment steps, without the need for a medical prescription, and without the need to use ingredients which cause skin irritations and other harmful side effects. Moreover, the shaving preparations of the present invention provide an additional advantage over the prior art in that they may be applied to the area to be shaved immediately prior to shaving, thus eliminating the need to apply the composition several hours prior to shaving.

SUMMARY OF THE INVENTION

The present invention includes improved shaving preparations for the treatment and prevention of PFB or ingrown hair containing glucocorticoid. The shaving preparation may also contain an antibacterial agent, as well as a therapeutic amount of benzoyl peroxide.

The present invention also includes a method for preventing and treating PFB, wherein the shaving preparations of the present invention may be applied to the skin area to be shaved immediately before shaving, as well as during, after and/or in between shaves.

DETAILED DESCRIPTION OF THE INVENTION

The present invention includes improved shaving preparations for the treatment and prevention of PFB. The present invention further includes methods for preventing and treating PFB, wherein the shaving preparations of the present invention are applied to the effected skin area immediately before shaving. In one embodiment of the present invention, the shaving preparation contains a therapeutic amount of a glucocorticoid. The glucocorticoid by itself avoids inflammation and provides mild thinning of the outer layer of the skin to help free ingrown hairs and to decrease the trapping of other hairs without the need to wait.

It is preferred to have the glucocorticoid present in the amount of about 0.025 to 2.5% by weight, and more preferably in the amount of about 0.05 to 1% by weight. In a most preferred embodiment of the invention, the glucocorticoid is present in the amount of about 1% by weight. The concentration of glucocorticoid in the shaving preparations of the invention differ depending on the particular glucocorticoid used.

Examples of glucocorticoids that may be used in the shaving preparations of the present invention are, for example, hydrocortisone USP, hydrocortisone acetate, desonide and triamcinolone acetate. Any other glucocorticoid may also be used in the shaving preparations. If the glucocorticoid is hydrocortisone USP, the preferred concentration is about 1 to 2.5% by weight. If using hydrocortisone acetate, the preferred concentration of glucocorticoid is about 1 to 2.5% by weight. If using desonide, the preferred concentration is about 0.05 to 0.1% by weight. For triamcinolone acetate, the preferred concentration is about 0.025 to 0.1% by weight. In an especially preferred embodiment of the present invention, the shaving preparation contains hydrocortisone USP in the amount of about 1% by weight.

In another embodiment of the present invention, the shaving preparation contains a therapeutic amount of glucocorticoid and an antibacterial agent. The antibacterial agent may be an antibiotic or a bacteriostatic agent. The antibiotic may be a keratolytic or non-keratolytic topical antibiotic, and is preferably present in the amount of about 0.5 to 5% by weight, and more preferably present in the amount of about 1 to 4% by weight. It is most preferred to have the antibiotic present in the amount of about 4% by weight.

A non-keratolytic topical antibiotic allows usage by those with sensitive skin because it does not cause irritation to the skin. Exemplary antibiotics that may be used in the shaving preparations of the present invention are bacitracin, polymyxin-B sulfate, and neomycin. However, any other antibiotic may also be used in the shaving preparations.

Bacteriostatic agents that may be used in shaving preparations of the present invention may be selected from, but are not limited to, the following: disodium edetate (EDTA), sodium metabisulfate, zinc sulfate, zinc oxide, and zinc phenosulfate, and combinations thereof. The bacteriostatic agent may be present in a therapeutic amount as recognized by those skilled in the art, typically in an amount of from about 0.005 to about 38% by weight. For example, disodium edetate may be used at a concentration of about 0.005 to about 0.1% by weight, preferably from about 0.008 to about 0.05%, and most preferably about 0.01% by weight. Sodium metabisulfate may used at a concentration of about 0.01 to about 1% by weight, preferably at about 0.05 to about 0.5%, and most preferably at a concentration of about 0.1%. For zinc sulfate, the concentration is typically in the range of from about 0.05 to about 3% by weight, preferably at about 0.1 to about 1%, and most preferably about 0.3%. For zinc oxide, the preferred concentration is from about 0.001% to about 38%. If using zinc phenosulfate, the bacteriostatic agent may be at a concentration of about 0.5 to about 5%, preferably about 0.5%.

In a further embodiment of the present invention, the shaving preparation contains a therapeutic amount of glucocorticoid, an antibacterial agent and a therapeutic amount of benzoyl peroxide. Benzoyl peroxide may also be included in the shaving preparations for use on those skin types most severely effected by PFB. It is preferred to have the benzoyl peroxide present in the amount of about 2.5 to 10% by weight, and more preferably in the amount of about 3 to 7%. It is most preferred to have the benzoyl peroxide present in the amount of about 5%.

The shaving preparation of the present invention is made by combining the ingredients together with a suitable carrier, such as a lotion, cream, or emulsion base. One example of a suitable carrier is white lotion NF (national formulary), which is made in a manner well-known to those skilled in the art. The shaving preparation of the present invention may also be made by combining the ingredients with a suitable foam or gel carrier, such as commercially available conventional shaving foams and gels. The shaving preparation may also be formulated in hardened form for application with a shaving brush. Alternatively, the shaving preparation of the present invention may be made by having towelettes or pledgets immersed in the preparation that can be applied to the area to be treated prior to, after or in between shaves.

Furthermore, additional ingredients, such as preservatives, emulsifiers, coloring agents, fragrances, thickeners, gelling agents, emollients, solvents and combinations thereof can be added to the shaving preparation of the present invention. Such additional ingredients may include for example, propylene glycol, which acts as a skin wetting and hair softening agent aiding in the prevention of hair re-entering the skin.

The shaving preparations of the present invention are further described with reference to the following non-limiting examples. These shaving preparations are combined in a manner well known to those of ordinary skill in the art.

EXAMPLE 1

A shaving preparation of the present invention containing the following ingredients: 2.5% by weight hydrocortisone acetate, 4% by weight bacitracin, 5% by weight propylene glycol, and the remainder being white lotion NF. Hydrocortisone USP may be substituted for the hydrocortisone acetate, and neomycin and/or polymyxin-B sulfate may be added to or substituted for bacitracin.

EXAMPLE 2

A shaving preparation of the present invention containing the following ingredients: 0.025% by weight triamcinolone acetate, 4% by weight bacitracin, 4% by weight propylene glycol, and the remainder being white lotion NF. Neomycin and/or polymyxin-B sulfate may be added to or substituted for bacitracin.

EXAMPLE 3

A shaving preparation of the present invention containing the following ingredients: 0.1% by weight desonide, 4% by weight bacitracin, 5% by weight propylene glycol, and the remainder being white lotion NF. Neomycin and/or polymyxin-B sulfate may be added to or substituted for bacitracin.

EXAMPLE 4

A shaving preparation of the present invention containing the following ingredients: 2.5% by weight hydrocortisone acetate, 4% by weight benzoyl peroxide, 5% by weight propylene glycol, with the remainder being white lotion NF.

EXAMPLE 5

A shaving preparation of the present invention containing the following ingredients: 2.5% by weight hydrocortisone USP, 4% by weight bacitracin, 3.5% by weight neomycin, 5% by weight polymyxin-B sulfate, 10% by weight benzoyl peroxide, 5% by weight propylene glycol, with the remainder being white lotion NF.

EXAMPLE 6

A shaving preparation of the present invention containing the following ingredients: 0.1% by weight desonide, 4% by weight bacitracin, 10% by weight benzoyl peroxide, 5% by weight propylene glycol, with the remainder being white lotion NF.

EXAMPLE 7

A shaving preparation of the present invention containing the following ingredients: 1.0% by weight hydrocortisone USP, 5% by weight propylene glycol, with the remainder being white lotion NF.

EXAMPLE 8

A shaving preparation of the present invention containing the following ingredients: 1% by weight hydrocortisone USP, with the remainder being a suitable carrier foam.

EXAMPLE 9

A shaving preparation of the present invention containing 1% by weight hydrocortisone acetate, with the remainder being white lotion NF, was used to treat a 33 year old female with a history of moderate to severe pseudofolliculitis barbae in the pubic area. The shaving preparation was applied to the affected area immediately prior to shaving one to two times per week. After two weeks of treatment, the number of lesions in the affected area were reduced by about 75 to 80%.

The shaving preparations of the present invention may be used on all areas of the body, preferably the face, neck and pubic areas. The shaving preparations of the present invention can be applied immediately prior to shaving, and used as a shaving cream. One of the advantages of the present invention over the prior art is that no waiting time is necessary between the application of the shaving preparation and shaving in order for the shaving preparation to be effective for the prevention and treatment of PFB. The shaving preparation of the present invention may be used in the exact manner as conventional shaving creams, foams or gels. Moreover, no unusual shaving procedures, such as removing trapped hairs mechanically using special instruments are needed when using the shaving preparations of the present invention. After first wetting the skin area to be shaved, a thin layer of the shaving preparation of the present invention is applied over the skin area. Then, the shaving preparation is removed by shaving the skin area using, for example, a conventional razor in a conventional manner. For additional reduction of inflammation and combating of infection, another application of the shaving preparation may be made after shaving.

The shaving preparation of the present invention can also be applied to the affected skin area several hours prior to shaving or in between shaves to aid in reducing inflammation.

The above mentioned features are exemplary in nature and are not to be construed as limitations of the present invention as set forth in the following claims. Persons skilled in the art will readily appreciate that variations from the description are possible without departing from the spirit and scope of the invention as defined in the claims.

I claim:

1. A method of aiding in preventing or treating pseudofolliculitis barbae consisting essentially of applying a shaving preparation wherein the active ingredient consists essentially of a therapeutic amount of a glucocorticoid to a skin area to be shaved, prior to shaving, after shaving, or between shaves.

2. The method of claim 1, wherein the shaving preparation comprises glucocorticoid provided in the amount of 0.025 to 2.5% by weight.

3. The method of claim 1, wherein the shaving preparation comprises a glucocorticoid selected from the group consisting of hydrocortisone USP, hydrocortisone acetate, desonide and triamcinolone acetate.

4. The method of claim 1, wherein the shaving preparation comprises hydrocortisone USP in the amount of about 1% by weight.

5. The method of claim 1, further comprising applying the shaving preparation after shaving.

6. The method of claim 1, wherein the shaving preparation is applied to the skin area between shaves.

7. A shaving cream to aid in the prevention or treatment of pseudofolliculitis barbae or ingrown hair wherein the active ingredient consists essentially of a therapeutic amount of glucocorticoid and a bacteriostatic agent selected from the group consisting of disodium edetate, sodium metabisulfate, zinc oxide and zinc phenosulfate.

8. A shaving cream to aid in the prevention or treatment of pseudofolliculitis barbae or ingrown hair wherein the active ingredient consists essentially of a therapeutic amount of glucocorticoid, an antibacterial agent and benzoyl peroxide.

9. A method of aiding in preventing or treating pseudofolliculitis barbae comprising applying a shaving preparation consisting essentially of a therapeutic amount of a glucocorticoid, propylene glycol and white lotion NF to a skin area to be shaved, prior to shaving, after shaving, or between shaves.

10. A method of hindering the appearance of pseudofolliculitis barbae consisting essentially of applying a shaving preparation wherein the active ingredient consists essentially of a therapeutic amount of a glucocorticoid to a skin area to be shaved, prior to shaving, after shaving, or between shaves.

11. A method of treating pseudofolliculitis barbae consisting essentially of applying a shaving preparation wherein the active ingredient consists essentially of a therapeutic amount of a glucocorticoid to a skin area to be shaved, prior to shaving, after shaving, or between shaves.

12. A method of aiding in preventing or treating pseudofolliculitis barbae comprising applying a shaving preparation wherein the active ingredient consists essentially of a therapeutic amount of a glucocorticoid to a skin area to be shaved immediately prior to shaving.

* * * * *